United States Patent
Simons et al.

(12)

(10) Patent No.: US 6,472,220 B1
(45) Date of Patent: Oct. 29, 2002

(54) METHOD OF USING CASSETTE OF LANCET CARTRIDGES FOR SAMPLING BLOOD

(75) Inventors: Tad Decatur Simons, Palo Alto; Michael Greenstein, Los Altos; Dominique Freeman, Pescadero; Leslie Anne Leonard, Portolla Valley; David A. King, Menlo Park; Paul Lum, Los Altos, all of CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/417,276

(22) Filed: Oct. 13, 1999

Related U.S. Application Data

(62) Division of application No. 08/985,299, filed on Apr. 12, 1997, now Pat. No. 6,036,924.

(51) Int. Cl.$^7$ ................................................ G01N 33/49
(52) U.S. Cl. ............................ 436/63; 436/808; 422/61; 422/100; 422/103; 422/104; 606/181; 606/182; 606/167
(58) Field of Search ............................ 422/61, 100–104; 438/808, 810; 606/181–182, 167

(56) References Cited

FOREIGN PATENT DOCUMENTS

WO          86-05966     * 10/1986

* cited by examiner

Primary Examiner—Lyle A. Alexander

(57) ABSTRACT

A cassette containing cartridges for sampling blood from a patient. The cassette includes a container for storing a plurality of cartridges and at least one cartridge in the container. The cartridge includes a cartridge case and a lancet. The lancet has a tip and is housed in the cartridge case. The lancet can be driven to extend the tip outside the cartridge case for lancing the skin of the patient to yield blood. The container has a compartment that contains at least one cartridge. A cartridge from the compartment can be loaded onto a glucometer that drives the lancet in the cartridge to lance the skin of a patient.

12 Claims, 10 Drawing Sheets

METHOD OF USING CASSETTE OF LANCET CARTRIDGES FOR SAMPLING BLOOD

CROSS REFERENCE TO RELATED APPLICATION(S)

This is a divisional of application Ser. No. 08/985,299 filed on Apr. 12, 1997 now U.S. Pat. No. 6,036,924.

FIELD OF THE INVENTION

The present invention relates to techniques for obtaining and analyzing blood samples, and more particularly to techniques for storing lancets that can be used for obtaining and analyzing blood samples in a convenient manner.

BACKGROUND

The analysis and quantification of blood components is an important diagnostic tool for better understanding the physical condition of a patient. Since adequate noninvasive blood analysis technology is not currently available, blood samples still need to be obtained by invasive methods from a great number of patients every day and analyzed. A well known example of such needs is self monitoring of glucose levels by a diabetic individual, e.g., performed at home. Many products for self monitoring of blood glucose levels are available commercially. Upon doctors' recommendations and using such products, patients typically measure blood glucose level several (3–5) times a day as a way to monitor their success in controlling blood sugar levels. For many diabetics, the failure to test blood glucose regularly may result in damage to tissues and organs, such as kidney failure, blindness, hypertension, and other serious complications. Nevertheless, many diabetics do not measure their blood glucose regularly. One important reason is that the existing monitoring products may be complicated, inconvenient, and painful, requiring a pin-prick every time a measurement is made. Furthermore, these products require some skill, dexterity, and discipline to obtain useful measurements.

Today, a diabetic patient who needs to monitor and control blood glucose levels typically carries the following paraphernalia: (1) a supply of disposable lancets, (2) a reusable lancing device which accepts the lancets, (3) an electronic glucose meter (glucometer), (4) a supply of disposable glucose test strips for the meter, and (5) tools for insulin injection (insulin, disposable hypodermic needles, and a syringe). These items may be carried in the form of a kit, which may also contain (6) a variety of control and calibration strips to assure the accuracy of the meter and the measurement. Examples of devices for monitoring blood glucose include GLUCOMETER ELITE glucose meter, Miles Inc. Elkhart, Ind., and ONE TOUCH PROFILE glucose meter, Lifescan Inc., Milpitas, Calif.

Using a typical glucose meter and lancing device, the sampling and measurement process is generally as follows. First, the user prepares the meter for use by removing a test strip from a protective wrapper or vial and inserting the test strip in the meter. This simple process requires some dexterity, since the test strips are very small, flexible, and can be damaged by accidentally touching the active sensing region. The glucose meter may confirm the proper placement of the test strip and indicate that it is prepared for a sample. Some glucose meters also may require a calibration or reference step at this time. Next, the patient cleans his finger when he intends to use the lancet—the finger is the preferred place for routine sampling, because it is an easily accessible place for most people. The user prepares the lancing device by (1) removing a cover from the lancing device, (2) placing a disposable lancet in the lancing device, (3) removing a protective shield from the sharp lancet tip, (4) replacing the cover, and (5) setting a spring-like mechanism in the lancing device which provides the force to drive the lancet into the skin. These steps may happen simultaneously, e.g., typical lancing devices set their spring mechanisms when one installs the lancet. The user then places the lancing device on the finger. (The density of nerve endings decreases toward the lateral edges of the fingertips; thus, slightly lateral locations are preferred to the fingertips.) After positioning the lancing device on the finger, the user presses a button or switch on the device to release the lancet. The spring drives the lancet forward, creating a small wound.

After lancing, a small droplet of blood may appear spontaneously at the lancing site, usually 2–20 $\mu l$ in volume. If no blood sample appears spontaneously, the patient may "milk" the finger by massaging or squeezing it slightly and thereby promoting blood flow from the wound. In either case the user examines the droplet of blood, judges by eye and experience whether the size of the sample is adequate for the chosen test strip (different test strips require different sample volumes). If adequate, the user quickly places the blood sample on a test strip (held in the glucose meter) according to manufacturer's instructions. Typically, the user inverts the finger to create a pendant drop and touches the drop (not the finger) to. an active region on the test strip that absorbs the blood. The action is difficult because inverting the finger over the test strip occludes the view of both the drop and the active region of the test strip. Furthermore, it is difficult to control the separation between the finger and the test strip which may be only a millimeter. Certain types of strip may require blotting and rubbing in a particular way. Another type of test strip draws the sample into the active region by capillary action. With this type, the user brings the sample in contact with a small opening on the test strip, and capillary action draws the sample volume into the test strip. Both types of strips (absorbent blots and capillaries) require that adequate sample volumes of blood exist on the finger before transferring the sample to the strip. One cannot apply more drops after the first application. This is because the principle of glucose measurement methods using current glucose meters depends on the rate of change in a chemical reaction, and the addition of additional sample confounds that rate and thus the calculation of glucose concentration. For convenience to the patient (user), it is desirable to have the entire droplet wick away from the finger onto the test strip, leaving the finger mostly free of blood. This is easier to accomplish with the capillary-fill test strips. The GLUCOMETER ELITE device has capillary-fill type test strips which require a few microliters of sample, only some fraction of which contacts the active sensor region.

After blood has been transferred to the test strip, the glucose meter then measures the blood glucose concentration (typically by chemical reaction of glucose with reagents on the test strip). Such blood glucose measurements permit the diabetic to manage his glucose levels, whether that be to inject a corresponding dose of insulin (generally Type I diabetic) or using a protocol established with his physician to modify his diet and exercise (Type I or Type II diabetic). Used lancets and test strips are removed and discarded (or kept for subsequent disposal in a hazardous waste container kept elsewhere). Any extra blood is cleaned from the equipment and the wound site, and all pieces of apparatus are stored for future use. The entire process usually takes a few minutes.

With the currently available blood glucose monitoring technology, a new lancet and test strip are used every time. The lancet and test strip are separate items, often purchased from different manufacturers. Furthermore, both are protected by a package or a protective shield, which must be removed before use, adding the requirement for dexterity. Because both are exposed to blood (considered a bio-hazard) they require careful or special disposal.

Each lancet prick causes pain. Among other considerations, pain from the lancet corresponds to the size of the wound, for a given location on the finger. A small lancet wound, which may cause less pain, may not provide enough blood for a sample, while a large wound may produce considerable pain and may clot slowly, causing great inconvenience to the user, who must take great care not to smear the leaking blood everywhere—clothes, work surfaces, glucometer, etc.—for some time thereafter.

From the above, it is clear that the conventional technique for blood sampling and analysis requires dexterity. Dexterity is required to load strips in a glucometer (unwrapping and inserting), as well as for positioning a small droplet onto the sensor surface of a test strip. Sample droplets are a few millimeters across and must be placed on similarly sized area of the test strip. This can be especially difficult for a weak, chronic or elderly diabetic patient, whose motions may be unsteady, vision compromised, or judgment impaired. Thus, the above prior systems are inconvenient and unpleasant to use. These shortcomings reduce the level of compliance of patients who need to perform these measurements assiduously.

Therefore, it is desirable to devise techniques of blood extraction and measurement that are easy to administer. What is needed are improved devices and methods for sampling and analyzing blood that require less mental concentration, less exertion, and less dexterity.

SUMMARY

This invention provides techniques for extracting a sample of human blood for the measurement of one or more of its constituents, such as might be used for routine monitoring of a chronic condition such as diabetes mellitus. The techniques of the present invention simplify the extraction and transfer of the blood sample, and reduce the inconvenience of the process. The techniques can be advantageously used in, for example, blood glucose monitoring as explained above.

In one aspect of the present invention, a cassette is provided for storing cartridges which can be used for sampling blood from the skin of a patient. The cassette has a cassette housing, i.e., a container, with room to hold a plurality of cartridges. When in use, the cassette contains at least one cartridge having a cartridge case and a lancet. The lancet has a tip and is housed in the cartridge case and operatively connected to the cartridge case such that the lancet can be driven to extend the tip outside the cartridge case for lancing the skin of the patient. The container has a compartment for storing at least one, but preferably many, cartridges. Alternatively many compartments can each contain one cartridge. A cartridge can be loaded from the cassette to a glucometer that can drive the lancet to lance the skin of a patient. In an preferred embodiment the cassette is associated with the driver so that the driver can be used to drive different cartridges of the cassette without having to remove the cassette from the glucometer. By keeping the cartridges, cassette, and the glucometer together, the process of lancing the skin is significantly simplified.

In an embodiment of the present invention, the technique of sampling blood utilizes a single unit for lancing and measurement (versus separate lancers and meters as in methods of prior technology) to significantly reduce the assortment of devices and supplies the user must carry. The glucometer of the present invention can accept a pre-loaded number of cartridges (with lancets) that are ready for use. In a preferred embodiment, the lancet and the analysis site for blood are in the same cartridge, further increasing the convenience of use. Using the blood sampling and analysis devices of the present invention, unlike the procedures used in conventional technology, the long list of steps required is significantly reduced. For example, after lancing, there is no need to return the package of lancet and the glucometer to storage separately. When the time for the next lancing arrives, there is no need to fumble for the lancet, lancing device and glucometer separately. Furthermore, the cassette can provide a convenient place for storing spent (i.e. used) cartridges, thereby facilitates easy disposal of spent cartridges and reduces the risk of blood contamination to others.

BRIEF DESCRIPTION OF THE DRAWINGS

The following figures are included to better illustrate the embodiments of the apparatus and technique of the present invention. In these figures, like numerals represent like features in the several views.

DETAILED DESCRIPTION

In one aspect of the invention, the present invention provides an apparatus—a cassette of cartridges—that can be used in conjunction with a lancing device that can drive the lancet of a cartridge. The cassettes of the present invention facilitate sampling blood safely, analyzing the blood sample conveniently, and disposing of the lancet and blood safely. In some preferred embodiments, using the lancet device, a patient can perform these sampling and analysis activities without touching the lancet by hand.

Cartridge

Cassettes for holding cartridges can be designed and made for a wide variety of cartridges in accordance with the present invention. For example, applicable cartridges include preferred embodiments of test cartridges in the copending U.S. Patent Application entitled "Lancet Cartridge for Sampling Blood," Ser. No. 08/985,384, filed on the same day and commonly assigned to the same assignee as the present application, are briefly described below. Said copending application is incorporated by reference in its entirety herein. These cartridges are described briefly here. It is to be understood that although test cartridges with analytical regions are described in detail herein, the present invention also is applicable for cartridges that do not have an analytical region, such as a cartridge having a chamber for storing blood after sampling.

An example of a cartridge suitable for use in the present invention includes a lancet, a cartridge case with an opening through which the lancet can protrude, and a test area associated to the cartridge case for analysis of blood. The lancet is mounted in the cartridge case in such a manner that (1) it can move with respect to the cartridge case and extend through the opening when forced by a separate actuator, and (2) when no actuating force acts on the cartridge, the lancet has a natural resting position completely inside the cartridge case (for example, constrained by a detent spring). Analysis can be done in the test area. An alternative is that a chamber can be used to store blood to be transferred to a separate analytical area from the test area. Further, it is to be understood that the cassettes of the present invention may be modified to accommodate other types of cartridges, and that other variations of the cassettes can be made to be used with other cartridges show described herein.

Flat Cartridge

Figure 1A:
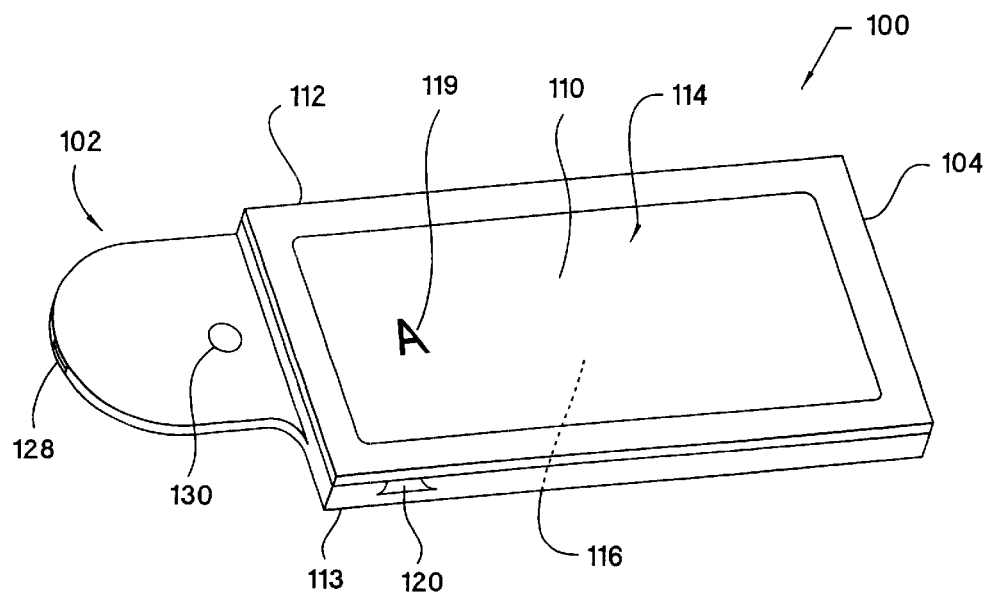
FIG. 1A shows an isometric view of an embodiment of the flat type of test cartridge of the present invention.
Figure 1B:
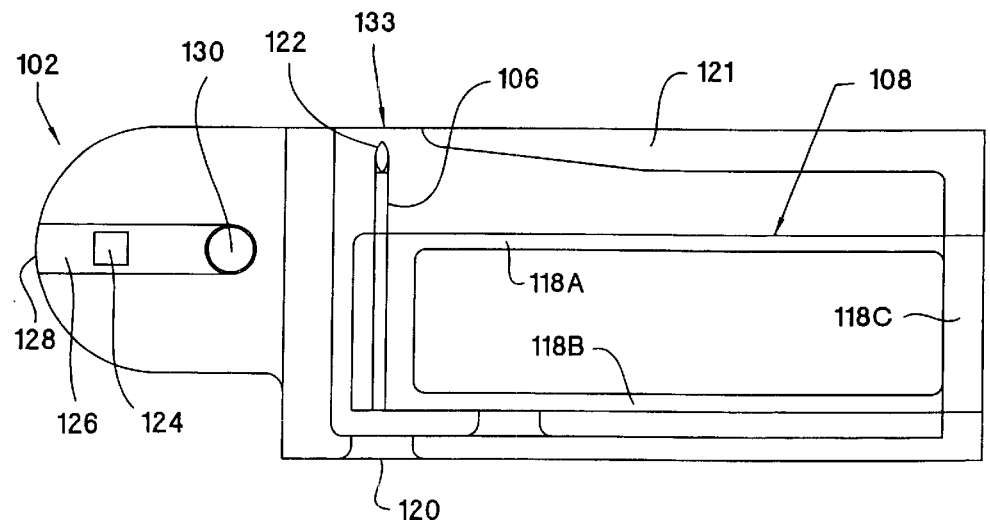
FIG. 1B shows a plan view of the test cartridge of FIG. 1A.

FIG. 1A shows an isometric view and FIG. 1B shows a plan view of an embodiment of a test cartridge that can be included in a cassette of the present invention. The test cartridge of FIG. 1A and FIG. 1B has a generally flat appearance, thus allowing many test cartridges to be stacked together for storage in the cassette. However, it is to be understood that other non-flat-shaped cartridges can also be used, so long as they can be stacked. For example, the cartridge can have two opposite surfaces each having a cross section that is curved, wavy, etc. to match the other surface. A test portion 102 protrudes from one side of the test cartridge 100. The test cartridge 100 can include a material for analysis of blood (see infra). The device 100 is referred to as a "test cartridge" because strips for analysis of blood in prior glucose meters are called "test strips" in the technical field. The test cartridge 100 has a cartridge case 104 integrally connected with the test area 102. A lancet 106 is connected to a cantilever lancet frame 108. The side of the cantilever lancet frame 108 remote to the lancet 106 is affixed to the cartridge case 104 whereas the side of the cantilever frame 108 near the lancet 106 is not affixed to the cartridge case 104. Thus, the lancet is operatively connected in the cartridge case 104 for movement. A covering 110 which has an absorbent material (for absorbing residual blood from the wound after lancing and testing) covers a surface (preferably the top surface) of the cartridge case 104. As used herein, the term "top surface" when used in connection with the generally flat test cartridge refers to the surface that is exposed for the most convenient access when the test cartridge is installed in association with a driver for lancing. Preferably, the top surface will face the same direction as the display of a glucometer when the test cartridge is loaded (or deployed) in the glucometer. Preferably, the cartridge case has a top face 114 on a top plate 112 and a bottom face 116 on a bottom plate 113 that are generally flat such that cartridges of this kind can be stacked one on top of another, and such that the covering material 110 can be conveniently used for wiping blood from the skin after lancing.

In this embodiment, as shown in FIG. 1B, the lancet 106 is mounted on a two-armed cantilever frame 108, the arms 118A, 118B of the cantilever frame 108 being about 20 mm long. A separate mechanism (e.g., an actuator rod not shown in the figures) inserted through a push port (or access hole) 120 can push the lancet 106 forward by acting against the part of the cantilever frame near the blunt end of the lancet 106. The lancet 106 at its distal end remote from the blunt end has a sharp tip 122 for penetrating the skin. As used herein, the term "distal" refers to a location or direction towards the skin during lancing. The term "proximal" refers to a location or direction that is opposite to "distal," near to the end of the lancet that is attached to the cantilever frame. The cantilever structure causes the lancet 106 to move in a generally straight direction (parallel to the lancet axis) with negligible curving or sideways motion, in order to pierce the skin with minimal tearing. In an at-rest state the lancet 106 resides about 0.5 mm proximal of the outside surface of the cartridge to prevent unwanted injuries. The lancet 106 is preferably 0.35 mm in diameter or smaller in order to not inflict a large wound.

When pushed, i.e., urged forward or actuated, the lancet 106 extends through the cartridge wall through an exit port 133. The lancet 106 will extend out of the distal side distal side of the lancing device through lancing hole 176, see FIG. 5. The cantilever arms 118A and 118B have a resilient property that, when the cantilever arms are bent, a tension develops to return (or spring) the lancet 106 to its at-rest position after lancing the skin and the actuating force on the lancet 106 is withdrawn (e.g., the actuator rod that inserts into the port 120 withdraws). The cartridge case 104 has a port 120 on the side of the cartridge case near to the blunt end of the lancet 106 for an actuator arm or rod (e.g., a push rod) to be inserted to push the lancet, thereby extending the lancet tip out the cartridge case 104. The maximal total travel of the lancet may be a few millimeters, limited by the interference (contact) of the cantilever lancet frame 108 and cartridge wall 121. The exact limit of travel of the lancet, which is important to minimize pain and injury, may be controlled by a mechanism which pushes the cartridge frame (which will be described later in the following). Each cartridge 100 may have an identifying mark 119 on the top surface 114 or absorbent cover 110. The identifying mark 119 can indicate the number of the cartridge (in a batch) or a special function (e.g., for a calibration cartridge). Further, special function cartridges can have a different color.

FIG. 1B is a plan view of the cartridge showing the test portion 102 and the lancet structure. The test portion 102 includes a test compartment (or test area) 124 depicted as a small square. As used here, the term "test compartment" refers to a space into which blood can pass and in which the property of the blood is sensed. A capillary passageway 126, for example, allows communication between a port (or entrance) 128 from which blood enters the test area 124. A vent hole 130 a distance (e.g., about 5 mm) away from the entrance 128 to the capillary, to the opposite side of the test area 124, terminates the capillary force to halt the filling of the capillary volume after pulling a blood sample over the active test area 124. As an alternative, a compartment without analytical capability can be used in place of a test area for storing blood. Such a compartment may have anticoagulants to prevent the blood from clotting.

In a preferred embodiment (although not clearly shown in FIGS. 1A and 1B), the test cartridge 100 has electrical contacts that allow for electrical communication with an instrument that processes a measurement (and perhaps controls the sensing) of an analyte (e.g., glucose) on the active test area. Such electrical contacts can be placed at a variety of locations on the test cartridge. Placing the contacts on the bottom (i.e., the side facing oppositely from the covering 110) permits a simple design and a simple interface to an instrument.

For analysis of the blood sampled, the test area 124 can contain chemicals that react with components of the blood samples. For example, enzymes that react with glucose can be present. The test area may also contain reagents that react with the iron present in the blood hemoglobin. Techniques, including electrochemical or spectroscopic techniques, that can be used for analysis of blood can be incorporated in the test cartridge 100. Examples of applicable analysis techniques can be found in, e.g., Tietz, Norbert W., Textbook of Chemical Chemistry, Chapter 6, pp 784–807, W. B. Saunders Co., Philadelphia, Pa., 1986, which are incorporated by reference herein. Test strips for analyzing glucose, pH, iron, and other common blood qualities are known in the art. For example, ONE TOUCH PROFILE diabetes tracking system commercially available from Lifescan Inc., Milpitas, Calif. 95035 has a unit that utilizes a strip for analyzing blood glucose and has an electronic system for displaying the result of analysis.

The top plate 112 or the top surface 110 may have a variety of useful markings that indicate which test cartridge is in use (in the case that the test cartridge is one out of many from a stack of test cartridges), and indication of batch or lot number of manufacture (for quality control and calibration), or that the cartridge is a special-purpose cartridge (e.g., for checking or calibration). (For comparison, some current lancing systems that make use of calibration strips are, e.g., GLUCOMETER ELITE glucose meter, Miles Inc. Elkhart, Ind., and ONE TOUCH PROFILE glucose meter, Lifescan Inc., Milpitas, Calif.).

Figure 2:
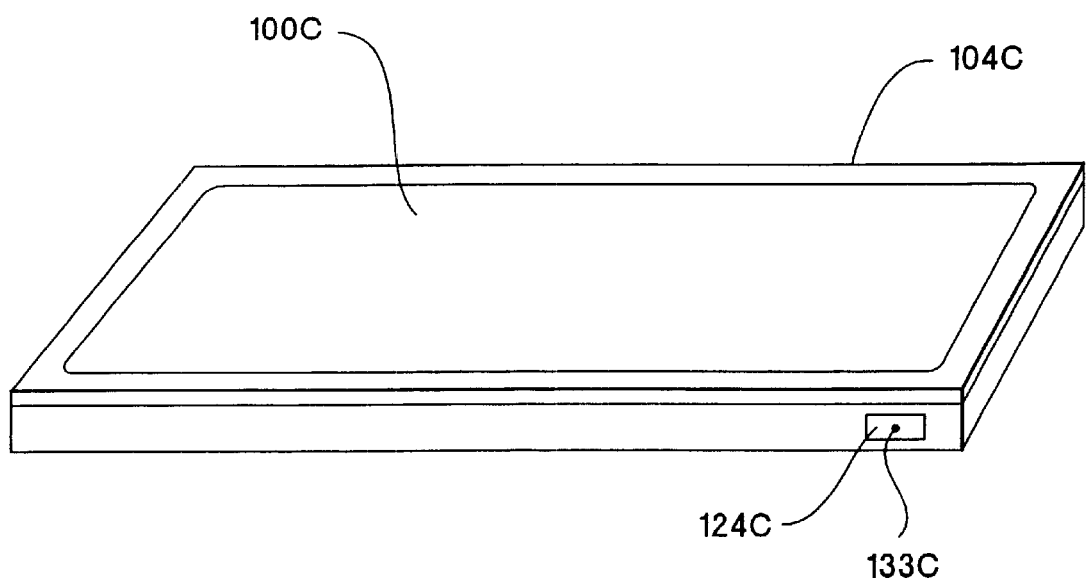
FIG. 2 shows an isometric view of another flat type test cartridge of the present invention.

Other embodiments of test cartridges are also applicable in accordance with the present invention, such as one with the test area 124 protruding at the a different side of the lancet area, or having a test area that resides directly neighboring the lancet 106 near the tip 122, so that the entrance (i.e., sample port) 128 to the capillary volume 126 and the exit port 133 for the lancet 106 are nearly coincident. This latter design enables the patient to lance the skin, and have the sample port for the test strip co-located for immediate filling. An example of such an embodiment is shown in FIG. 2. The test cartridge 100C has a test area 124C that is at the immediate vicinity of the lancet exit port 133C, which in this embodiment is a hole. The test area 124C can be a sensing surface surrounding the lancet exit port 133C. Preferably the test area 124C is set back slightly from the distal side of the cartridge case 104C so as to avoid inadvertent contact with skin or other objects. When the skin is lanced and a drop of blood appears, the drop of blood can reach beyond the set back distance to contact the test area 124C.

Bar-Shaped Cartlidge

Figure 3A:
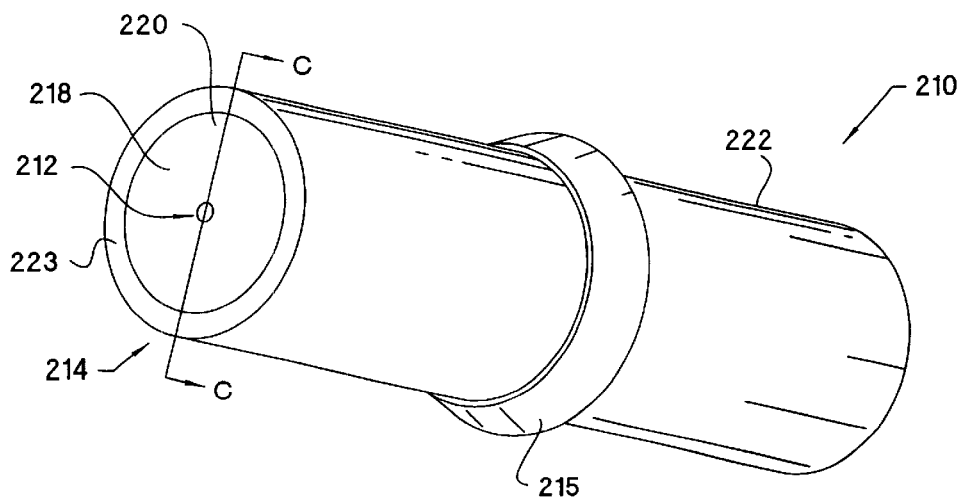
FIG. 3A shows an isometric view of a bar-shaped test cartridge of the present invention.
Figure 3B:
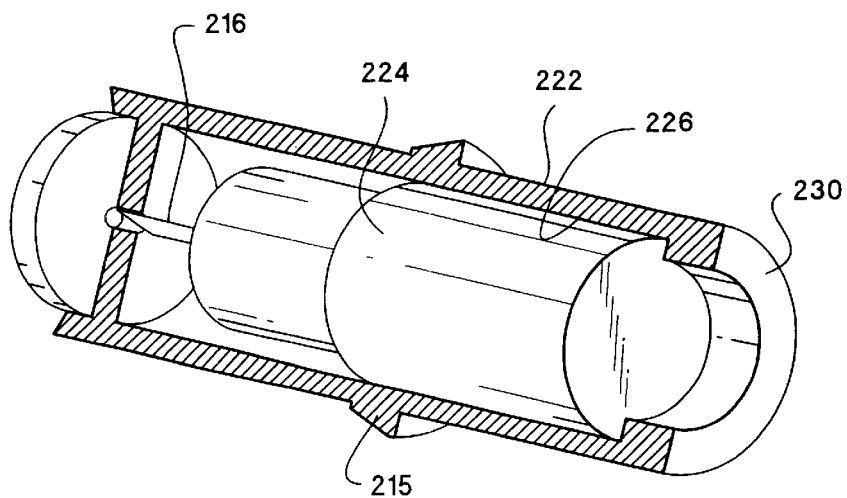
FIG. 3B shows an exploded isometric view in portion of the test cartridge of FIG. 3A.

FIGS. 3A to 3D show an embodiment of a bar-shaped test cartridge that can be included in a cassette. The test cartridge has a lancet and a blood analyzer, i.e., sensor (such as a blood chemistry test strip that can determine glucose level) and which can be mounted easily into a driving instrument (driver). The overall lancing device operates with the test cartridge to gather a blood sample in a single operation and simplifies the measurement procedure. FIG. 3A shows an isometric view of the embodiment of the test cartridge 210, about 6 mm in diameter and 15–20 mm in length. FIG. 3B shows an isometric view, cut-out in portion, of the test cartridge 210 of FIG. 3A. For comparison, the size and shape is similar to that of the ULTRAFINE lancets of the Becton-Dickinson Co. It is noted that, although the bar-shaped test cartridge 210 has, preferably, a round cross-sectional shape, it can also have other regular cross-sectional shapes, such as oval, square, rectangle, rhombus, triangle, etc. An aperture 212 (or lancet exit hole) is located at a distal end 214 of the test cartridge 210. A lancet 216 is housed at rest inside the test cartridge 210 proximal of (i.e., beneath if considering the distal end as facing upwards) the aperture 212, which has a diameter slightly larger than the lancet 216 (~0.35 mm diameter). The lancet 216 can pass through the aperture 212 when actuated for lancing. Herein, when referred to a bar-shaped test cartridge, "top," and "up" refer to a direction or location towards the skin to be lanced, i.e., towards the distal end. The material 218 around the aperture can be an absorbent material which serves to soak up blood after lancing. The absorbent material, or the surface beneath it, can also serve as the active test area 220 for measurements of blood characteristics, such as glucose level. As in existing glucose measurement techniques, a chemical reaction occurs when blood contacts the test area 220, and thus, for example, indicates the presence and amount of glucose. The test area 220 can generate an electrical signal that is conducted from the test area 220 (preferably via conductors molded into the case) to electrical contacts (not shown) on the cartridge case 222. The test cartridge case 222 has a lip 223 protruding slightly out distally at the distal end 214. The protruding lip 223 results in a small void area protecting the test area 220 from being inadvertently touched. As used herein, the meaning of the term "compartment" when referred to the space for receiving blood also can include the space encircled by the lip 223. FIG. 3B is a projected sectional view in portion of the cartridge, showing the cartridge case 222, the lancet 216, and the absorbent material 218 distal to the lancet 216 when at rest. The lancet 216 is mounted on a cylindrical lancet mount 224. The cartridge case 222 has a cylindrical internal wall 226 upon which the lancet mount 224 can slide.

Figure 3C:
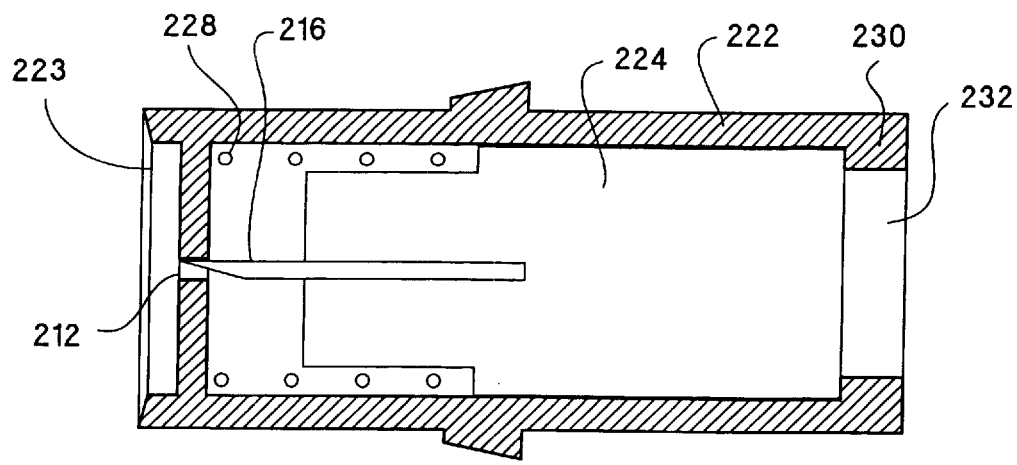
FIG. 3C shows a sectional view along the axis of the bar-shaped test cartridge of the present invention.
Figure 3D:
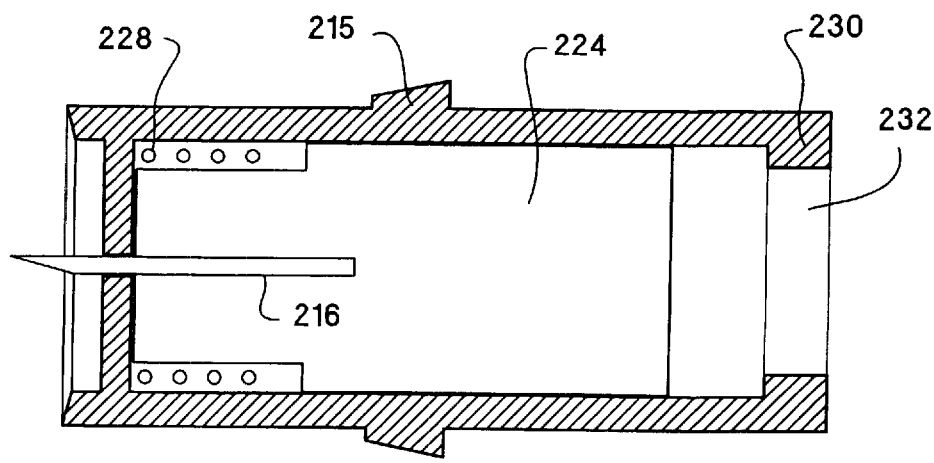
FIG. 3D shows a sectional view of the test cartridge of FIGS. 3A–3B, showing the lancet extended for lancing.

FIGS. 3C and 3D are sectional views of the test cartridge 210 along the plane C—C of FIG. 3A. Shown in FIGS. 3C and 3D (but not in FIG. 3B for clarity) is a retaining spring 228 which compresses the lancet mount 224 against the bottom 230 of the test cartridge 210. A large bore 232 on the bottom 230 of the cartridge case 222 permits an external actuator (not shown in FIGS. 3A to 3D) to extend through-to act on the lancet mount 226. FIG. 3C shows the test cartridge 210 at rest, with the lancet 216 residing beneath the aperture 212 and the absorbent surface 218. When an external actuator (not shown) acts through the bottom bore 232 against the lancet mount 224, the cartridge spring 228 is compressed and lancet 216 will emerge through the aperture 212 where it can pierce a patient's skin. See FIG. 3D. When the actuator force is removed, e.g., by withdrawal of the actuator, the resilient nature of the cartridge retaining spring 228 returns the lancet 216 to the at-rest position inside the cartridge case 222. In this manner, the lancet 216 is only exposed during lancing. Therefore, the user is protected against unintentionally inflicted wounds and scratches, and also from exposure to the contaminated lancet. With prior technology, accidental lancet pricks can occur more easily.

B. Cassette Containing Several Cartridges.

Cassette for Flat Cartredges

Figure 4A:
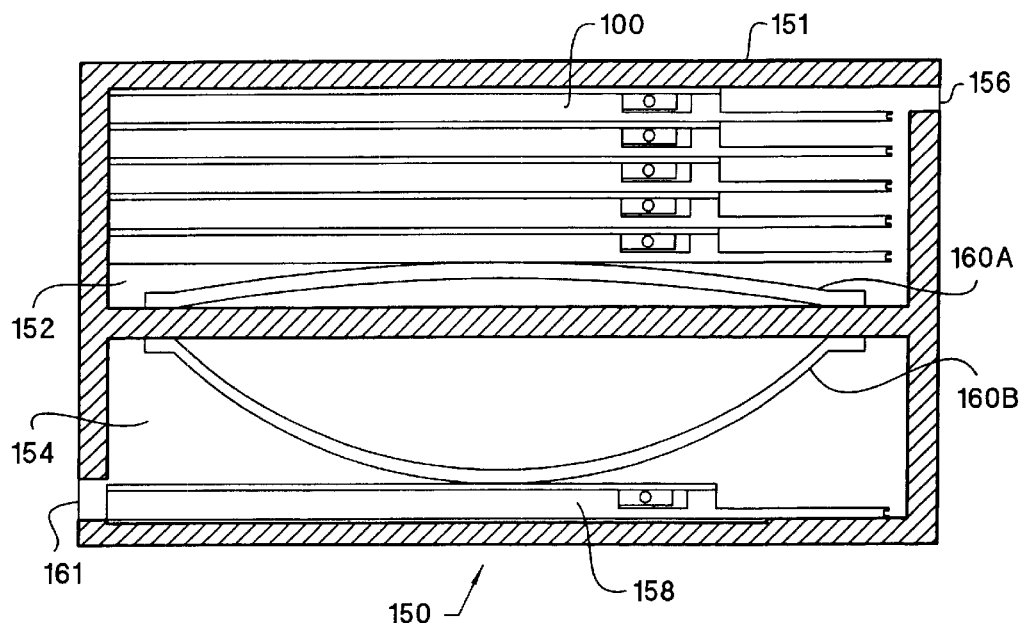
FIG. 4A shows a plan side view of a cassette of test cartridges of the present invention.

In the embodiment shown in FIGS. 1A and 1B, the cartridge has a generally thin and flat shape. The thin, flat design of the cartridges permits several cartridges to be packaged (in a stack) in a small cassette, similar in design to existing dispensers of single-edged razor blades. A side view of an embodiment of a cassette of test cartridges according to this invention is shown in FIG. 4A. In this figure, the cassette 150 has a container 151 and includes an upper chamber (or compartment) 152 filled with new (i.e., unused) test cartridges 100 ready for use and includes a lower chamber 154 for optional storage of spent cartridges 158. It is desirable that the spent test cartridge be isolated since it contains blood products. The lower chamber 154 allows for efficient, contained disposal of spent test cartridges by the user. A curved spring (160A or 160B) in each chamber holds the test cartridges in place. The upper spring 160A in the upper chamber 152 also pushes the new cartridges 100 to the top of the cassette 150 for easy dispensing. The cassette 150 also serves to keep the supply of new test cartridges clean and properly oriented in anticipation of their use, as well as helps to maintain the sterility of the test cartridges.

Figure 4B:
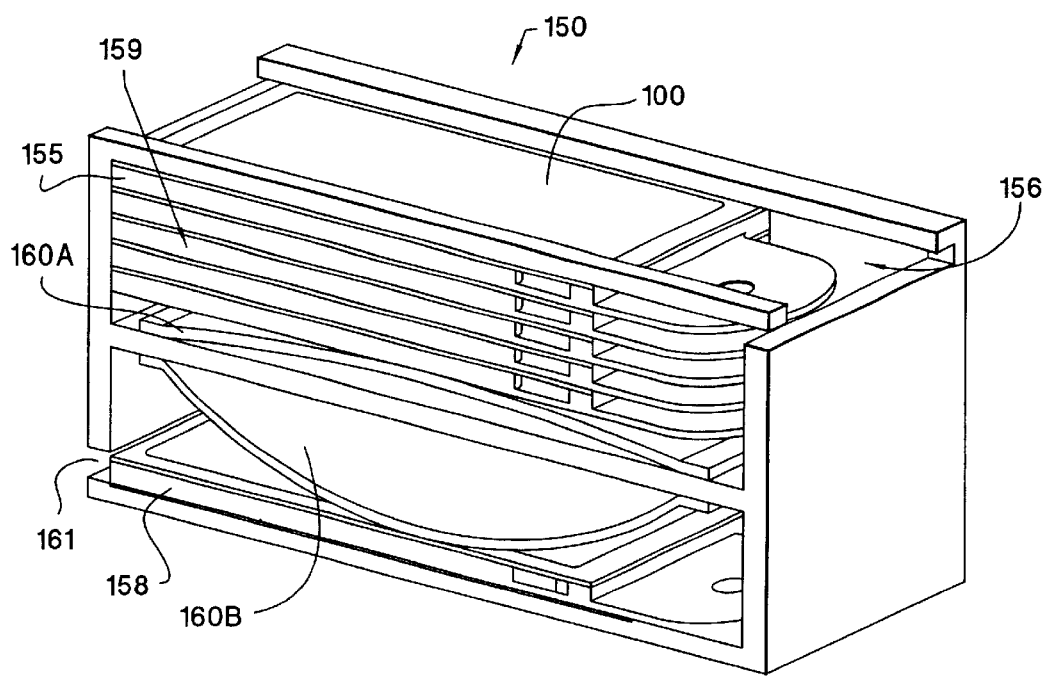
FIG. 4B shows an isometric view of the cassette of FIG. 4A.

FIG. 4B shows an isometric view of the assembled cassette with an exit port (or opening) 156 on the top surface through which new test cartridges may be ejected. As used herein the term "top" when referring to the cassette means the side with the new test cartridges and where the test cartridge next to be deployed is loaded. A sweeper (e.g., with an arm reaching to the end of the top test cartridge 155 in the cassette remote to the exit port 156 can, with a sweeping motion, push a test cartridge to slide from the stack of new test cartridges out the exit port 156. A practical cassette would hold multiple test cartridges, e.g., 8 to 30 preferably, an adequate supply for 2–7 days, depending on usage. Similarly, the chamber 154 for storing spent test cartridges also has an entrance port 161 through which a spent cartridge can be inserted manually. Preferably, the cassette 150 has a transparent window on the upper half 159 (not shown in FIGS. 4A and 4B) through which the number of remaining unused cartridges in the cassette can be determined. If the glucometer has a wall that covers the transparent window 159 then that wall of the glucometer is preferably transparent as well to allow the user to see the test cartridges in the cassette.

Figure 5A:
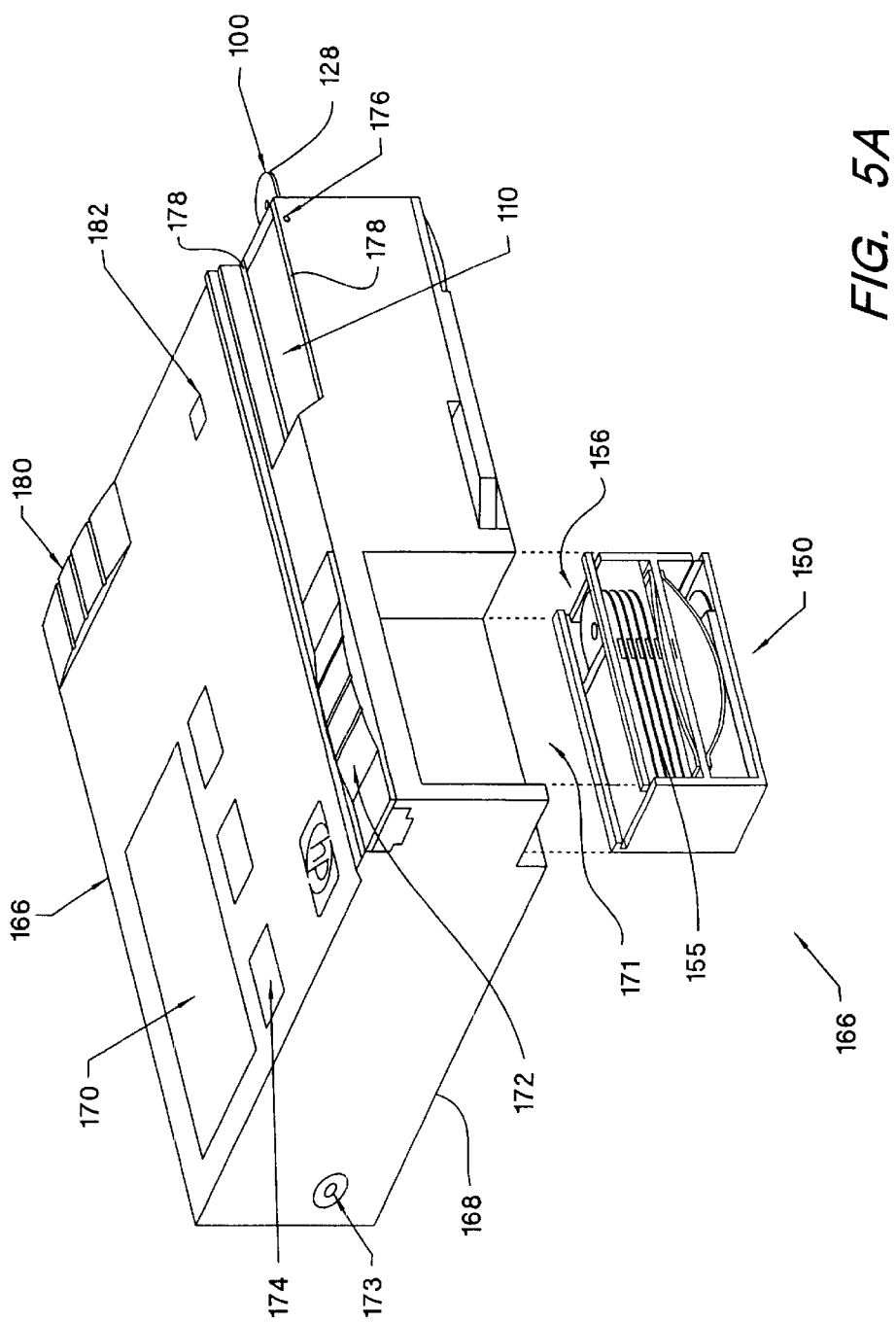
FIG. 5A shows an exploded view in portion of a glucometer of the present invention, showing a cassette with flat type test cartridges.
Figure 5B:
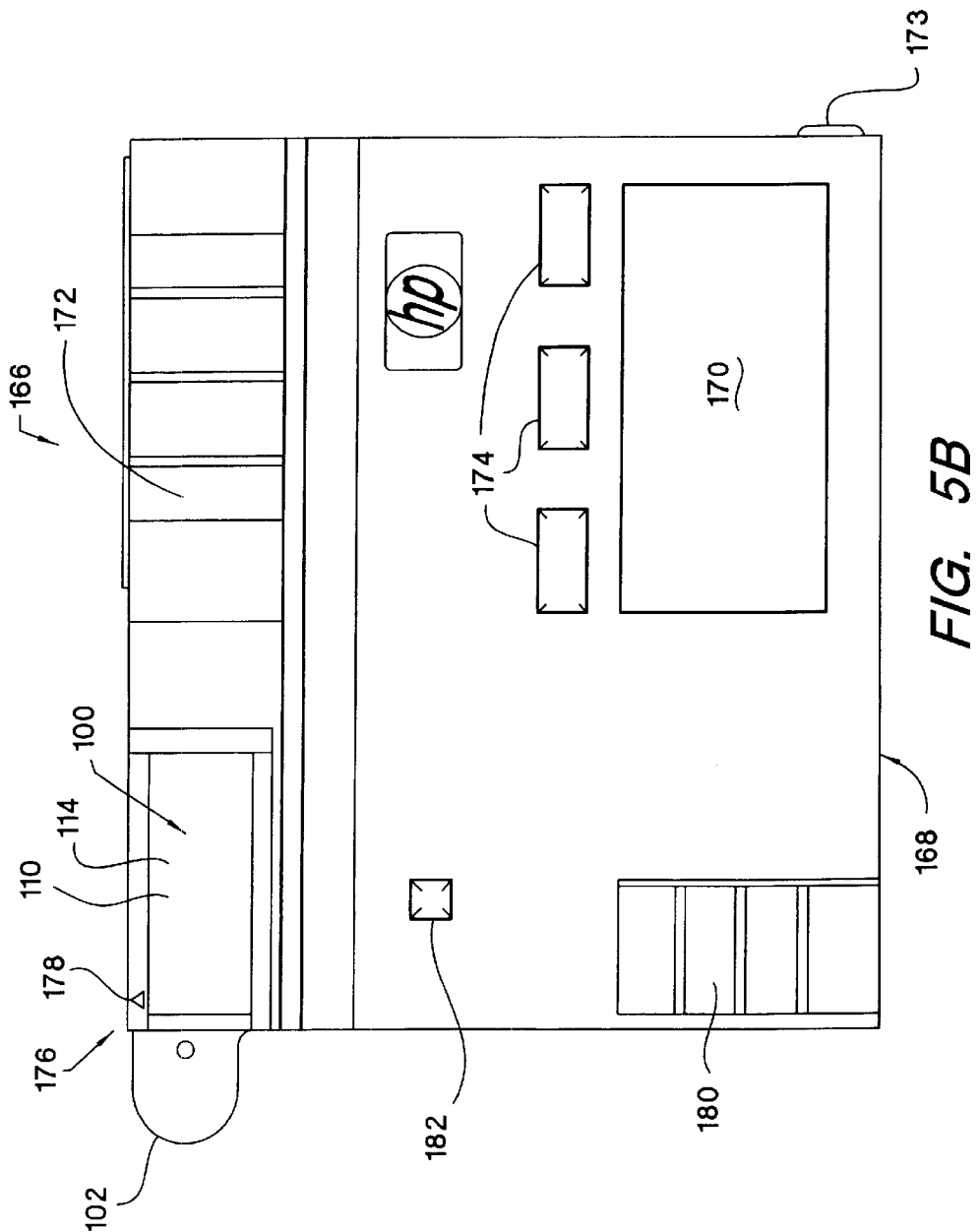
FIG. 5B shows a plan view of a glucometer of FIG. 5A.

FIG. 5A is an isometric view showing an embodiment of how a cassette containing flat test cartridges similar to those described above can be inserted into an instrument (glucometer) that can process the sample and display data. FIG. 5B shows a plan view of the glucometer. In the embodiment shown in FIG. 5A and FIG. 5B, the glucometer 166 has a body 168 that has a recess 171 for receiving and securing a cassette 150. The recess 171 is adjacent to a sweeper 172 that advances individual cartridges into a position for use. As described earlier, the sweeper 172 can have a pusher finger that reaches to the end of the top test cartridge 155 in the cassette remote to the exit port 156 and, with a sweeping motion, can push the top test cartridge to slide from the stack of new test cartridges out the exit port 156. Alternately, test cartridges may also be loaded individually without a cassette. The sliding mechanism of the sweeper 172 is similar to a dispenser of single-edged razor blades. The proper, loaded, position results in the test portion 102 of a test cartridge protruding from the body 168 of the glucometer). The same mechanism can eject the test cartridge after use for proper disposal.

The body 168 of the glucometer 166 further has electronic circuits including a processor (which is not shown) to control and read the results of an analysis using the test cartridge, electrical data port 173, and control buttons for control, communication, programming, and set-up of the instrument (setting date, time, language preference, scrolling through stored values, on/off settings, instrument diagnostics, etc., as well as sending or receiving information to electronics external to the body).

FIG. 5A also shows a test cartridge 100 in place for use, with the sample port 128 of the cartridge protruding from the glucometer. As shown in FIG. 5B, the test portion 102 (with the sample port 128 being most remote from the body 168) sticks out from the body. Additionally, preferably, a test cartridge is loaded in the body of the glucometer such that the test cartridge has an exposed top surface (see FIG. 5B). The exposed top of the test cartridge has an absorbent area for wiping excess blood from the finger if necessary at the end of a test. Furthermore, a mark 178 can be molded or printed into the glucometer to show the location of the lancet hole 176 (corresponding to the location of the finger for lancing) through which the lancet will protrude to lance the skin of a patient.

To provide a driving (or actuating) force to push the lancet for lancing, a cockable actuator 180, e.g., one that contains a sliding lever for cocking a spring-activated (the spring and the puncher are not shown) puncher can be used. After cocking the spring in preparation for lancing, a button 182 can be pressed to or release the spring-activated puncher to drive the pre-loaded lancet. As a result, the lancet tip is driven to extend out of the test cartridge 100. Spring actuated cockable mechanisms are know in the art. The present cockable actuator is similar to those found in existing lancing devices, but is integrated into this instrument housing. The lancing button 182 preferably is located away from the control buttons 174 and has a different color, and markings, for preventing from being activated inadvertently.

To illustrate the use of the embodiment of the glucometer of FIGS. 5A and 5B, for example, a test cartridge 100 is loaded (or deployed) in the glucometer 166 and the spring-actuated driver is cocked to get the glucometer ready to lance a finger. When the cocked driver is released, the driver pushes the lancet to lance the finger. After a lancet has pierced the lateral edge of a finger successfully, a convenient way to educe blood from the wound site is to press gently on the fingertip near the wound where the tissue is soft. A gentle push for a second will promote a few microliters of blood to appear as a stationary droplet (to get a droplet of a 2–20 μl, which is a sufficient sample for glucose measurements). With a small wound, the lack of spontaneous bleeding after testing is also convenient to the patient because no messy, leaking wound remains, which can soil objects or can require protection. Also, the residual scarring is minimal, which is helpful if the patient must return to the same site later for additional samples—a problem with patients who make frequent tests.

The droplet of blood can be exposed to sample port 128 and transferred to the test area 124 to be analyzed. Result of the analysis is transferred electrically through electrical contacts, wires, and connections to the processor. After analysis and data collection, the spent test cartridge can be ejected and stored in the chamber 154 for spent cartridges in the cassette 150.

Cassette for Bar-shaped Cartridges

Figure 6A:
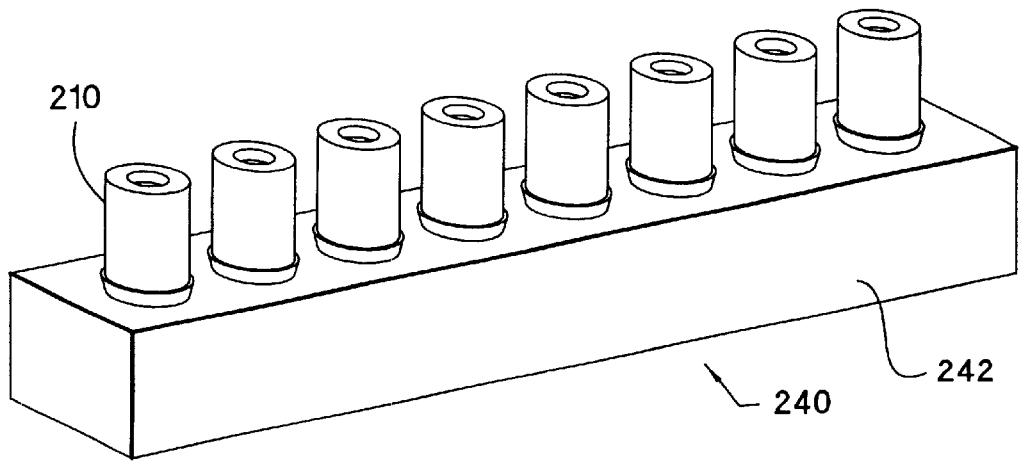
FIGS. 6A and 6B show an embodiment of a cassette with bar-shaped cartridges.
Figure 6B:
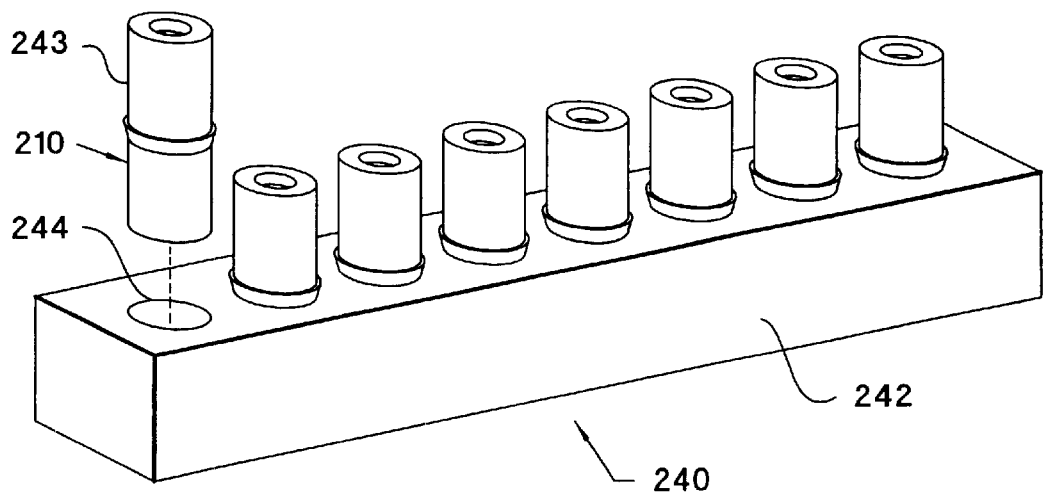
Figures 6C, 6D:
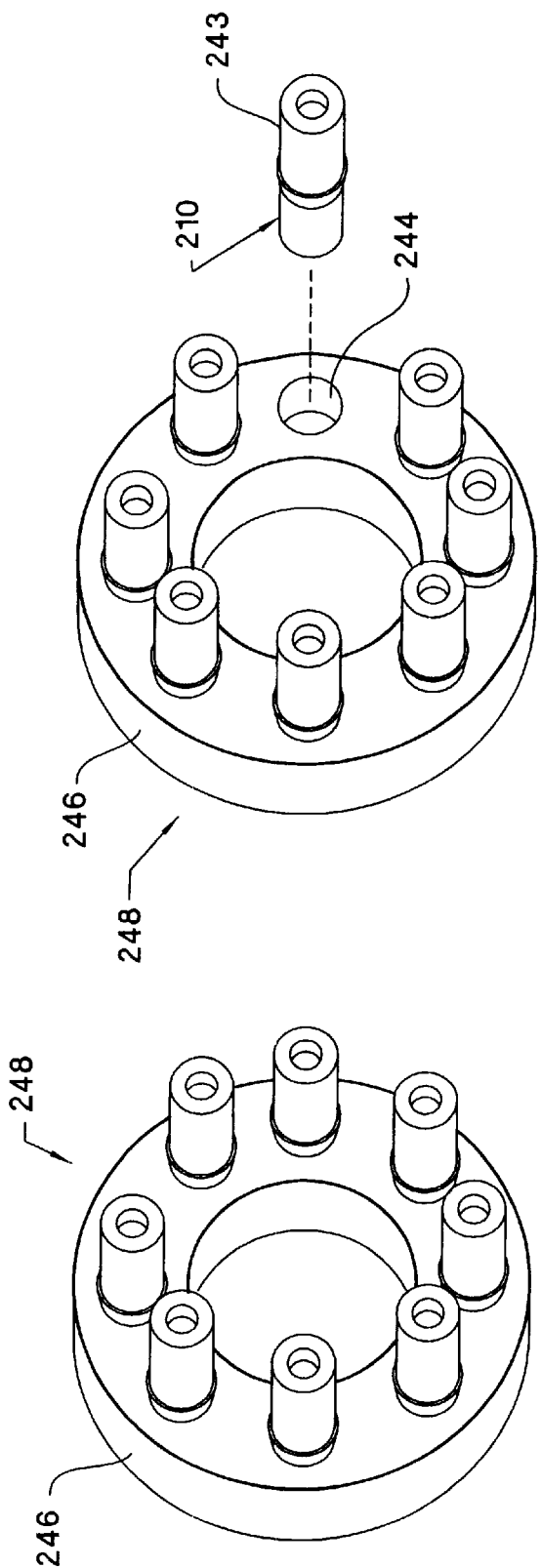
FIGS. 6C and 6D show another embodiment of a cassette with bar-shaped cartridges.

FIGS. 6A and 6B shows an embodiment of a cassette of bar-shaped test cartridges of FIGS. 3A to 3D. The cassette 240 has a cartridge holder 242, which has a plurality of cavities 244 arranged, here shown linearly, in each of which a test cartridge 210 can fit. Preferably the distal portion 243 of the test cartridge 210 fits into the cavity 244 snugly. In another embodiment shown in FIGS. 6C and 6D, the cartridge holder 246 in the cassette 248 is ring-shaped. A cartridge in one of these cassettes can be dislodged from the cavity 244 and inserted into a lancing device.

In general, a lancing device having a driver with a cocking and release mechanism including a release button can be used for driving the test cartridge. Such mechanisms with release buttons are known in the art. Examples of a lancing device that can be used in conjunction with the test cartridges and cassettes of the present invention are described in copending application copending U.S. patent application Ser. No. 08/985,307, entitled "Integrated System and Method for Blood Sampling and Analysis," and copending U.S. patent application Ser. No. 08/985,303, entitled "Reproducible Lancing for Sampling Blood," filed on the same day and commonly assigned to the same assignee as the present application, said copending applications are incorporated by reference in their entirety herein.

Figure 7A:
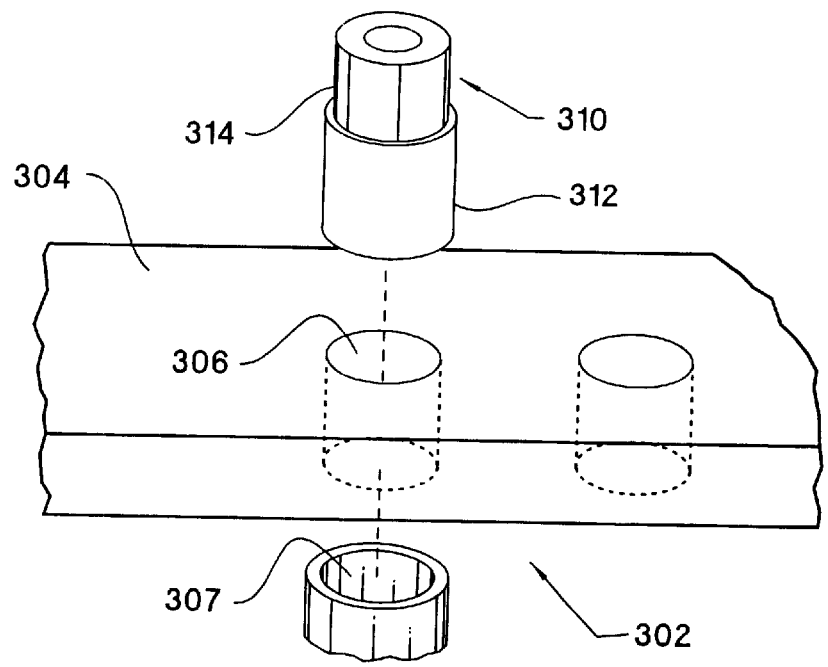
FIG. 7A shows an embodiment of a cassette for bar-shaped cartridges suitable for used with a driver nearby.

FIG. 7A shows an embodiment of a cassette with test cartridges suitable for use with a driver nearby. In this embodiment of a cassette 302 (shown in portion), the test cartridge holder 304 has a plurality of throughholes 306 into each of which a test cartridge's 310 proximal portion 312 snugly fits. A driver 305 (shown in portion), is positioned immediately underneath, i.e., proximal to, the throughhole 306 of test cartridge holder 304 such that the test cartridge 310 can be pushed into the receiving cavity 307 of the driver 305. When deployed in the driver, the distal portion 314 of the test cartridge 310 still protrudes distally of the test cartridge holder 304 adequately such that the test cartridge can be conveniently used for lancing. After lancing, an arm or a similar device (not shown) may be used to push the proximal end of the test cartridge out of the receiving cavity in the driver back into throughhole 306. Alternatively, a grip (not shown) can be used to pull the distal portion 314 of the test cartridge 310 back into the throughhole 306. The test cartridge holder 304 can be linear, ring-shaped, or other shaped so long as it can be maintained in the immediate vicinity of the driver.

Figure 7B:
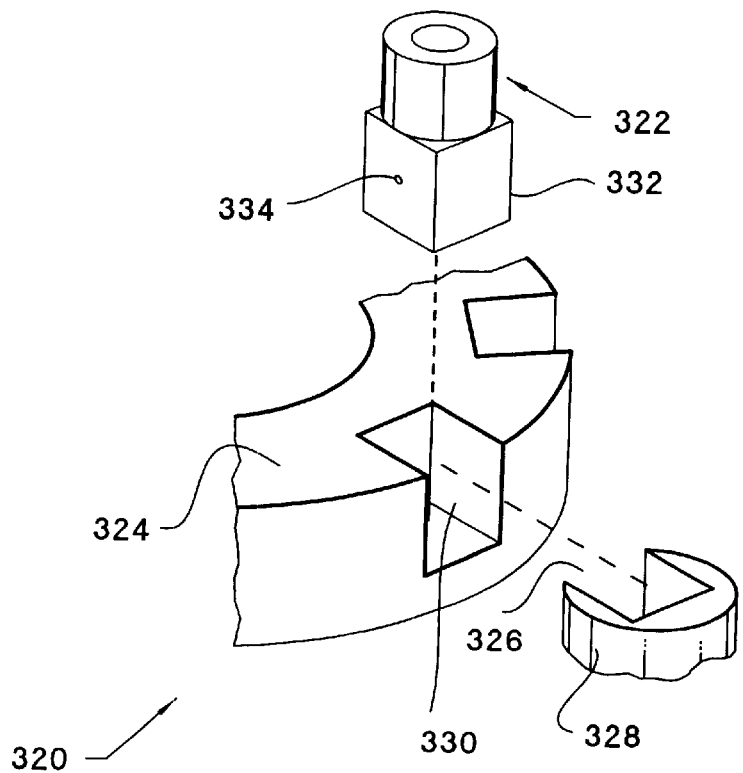
FIG. 7B shows another embodiment of a cassette for bar-shaped cartridges suitable for used with a driver nearby.

FIG. 7B shows another embodiment of a cassette 320 in which a test cartridge 322 can be slid (i.e., transferred) off the test cartridge holder 324 into a cartridge holding cavity 326 of a driver 328. The cartridge holder 324 has a plurality of holding cavities 330 in which test cartridges can be stored. On the cartridge holder 324, a side the normal of which is perpendicular to the axis of the test cartridge 322 is open so that a test cartridge 322 can be slid in or out of the holding cavity 330. Similarly, the cartridge holding cavity 326 of the driver 328 has an open side into which the test cartridge 322 can slide to be held by the driver. The proximal portion 332 of the test cartridge 322, the holding cavity 330 of the cartridge holder, and the cartridge holding cavity 326 of the driver 328 all have planar walls to facilitate the sliding action of the test cartridge in the cavities. Depressions 334 on the side of the planar side walls of the proximal portion 332 of the test cartridge 322 can be present to correspond to pins or springs on the planar side walls of the cartridge holding cavity 326 of the driver 328 to help retain the test cartridge 322 therein. The test cartridge 322 can be slid by means of an arm from the cassette 320 to the driver 328 before lancing. After lancing, the test cartridge 322 is slid back into the cassette 320 before disposal. In the embodiment shown in FIG. 8B, the cassette test cartridge holder 324 is ring-shaped and can be rotated to position a new test cartridge to face the driver after a test cartridge has been used.

Although the preferred embodiment of the present invention has been described and illustrated in detail, it is to be understood that a person skilled in the art can make modifications, especially in size and shapes of features within the scope of the invention.

What is claimed is:

1. A method for sampling blood from the skin of a patient for analysis, comprising:
    (a) providing a cassette containing a plurality of test cartridges, the at least one test cartridge having a lancet having a tip shielded in the test cartridge;
    (b) inserting the cassette into a driver; and
    (c) deploying one of the at least one test cartridge to associate with the driver and driving the lancet to extend the lancet tip out of a test cartridge such that the lancet pierces the skin to yield blood.

2. The method according to claim 1 further comprising transferring a test cartridge from the cassette to be held in a support to associate with the driver.

3. The method according to claim 1 further comprising deploying a test cartridge in the support for lancing by transferring the test cartridge from the cassette to associate with the driver by a mechanical arm without requiring the test cartridge to be touched by hand.

4. The method according to claim 1 wherein the cassette further comprises a second compartment for receiving one or more spent test cartridges.

5. The method according to claim 1 further comprising including in the cassette at least two test cartridges each having a cartridge case with an identification mark visible while the test cartridge is in the cassette, from which identification mark a characteristic,of the at least on test cartridge in the cassette is determinable.

6. The method according to claim 1 further comprising loading from the cassette to the actuator a calibration cartridge to calibrate the at least one test cartridge in the cassette.

7. The method according to claim 1 wherein the at least one test cartridge includes two surfaces on opposite sides to facilitate stacking test cartridges together in the cassette.

8. The method according to claim 1 wherein the cassette includes an axis upon which the cassette can revolve to expose a test cartridge for use.

9. The method according to claim 1 wherein the cassette includes slots for holding bar-shaped test cartridges and the at least one test cartridge is barshaped having a cartridge axis parallel to which the lancet can extend.

10. The method according to claim 1 wherein the test cartridge has no detachable cover shielding the lancet and wherein the cartridge case shields the lancet from being touched by the patient before being driven to extend, the lancet being returnable into the cartridge case after lancing the skin.

11. The method as claimed in claim 1, including returning the at least one test cartridge to the cassette after the lancet pierces the skin to yield blood.

12. A method for sampling blood from the skin of a patient for analysis, comprising:
    (a) providing a cassette containing two or more test cartridges in a stacked position, the two or more test cartridges each having a lancet having a tip shielded in the test cartridge;
    (b) removing one of the test cartridges from the stacked position and deploying the test cartridge to associate with a driver and driving the lancet to extend the lancet tip out of a test cartridge such that the lancet pierces the skin to yield blood; and
    (b) removing the test cartridge from the driver and place the test cartridge into a compartment for disposal.

* * * * *